(12) United States Patent
Ishizaki et al.

(10) Patent No.: US 9,392,932 B2
(45) Date of Patent: Jul. 19, 2016

(54) ENDOSCOPE

(71) Applicant: Olympus Corporation, Tokyo (JP)

(72) Inventors: Ryosuke Ishizaki, Tama (JP); Hiroaki Miyoshi, Fuchi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/142,642

(22) Filed: Dec. 27, 2013

(65) Prior Publication Data

US 2014/0187865 A1 Jul. 3, 2014

Related U.S. Application Data

(63) Continuation of application No. PCT/JP2013/060492, filed on Apr. 5, 2013.

(30) Foreign Application Priority Data

Apr. 12, 2012 (JP) .................................. 2012-090894

(51) Int. Cl.
*A61B 1/00* (2006.01)
*A61B 1/005* (2006.01)
(Continued)

(52) U.S. Cl.
CPC ............. *A61B 1/0057* (2013.01); *A61B 1/0052* (2013.01); *A61M 25/0136* (2013.01);
(Continued)

(58) Field of Classification Search
CPC .. A61B 1/0051; A61B 1/0057; A61B 1/0052; A61M 25/0136; A61M 25/0147
USPC ......... 600/114, 125, 138, 139, 144, 146, 148, 600/149, 141, 142, 104, 434, 585; 604/95.02, 95.03, 95.04, 523, 528
See application file for complete search history.

(56) References Cited

U.S. PATENT DOCUMENTS 3,892,228 A 7/1975 Mitsui
6,440,062 B1 * 8/2002 Ouchi .......................... 600/146
(Continued)

FOREIGN PATENT DOCUMENTS

JP U1-49-80087 7/1974
JP A-60-48725 3/1985
(Continued)

OTHER PUBLICATIONS

May 14, 2013 International Search Report issued in International Patent Application No. PCT/JP2013/060492 (with translation).
(Continued)

*Primary Examiner* — Anhtuan T Nguyen
*Assistant Examiner* — Timothy J Neal
(74) *Attorney, Agent, or Firm* — Oliff PLC (57) ABSTRACT

An endoscope includes an insertion section including first and second bending portions, a first bending drive mechanism to bend the first portion in the upward direction, first and second distal side-traction members passing inside the insertion section and a proximal side-traction member. The first portion can bend in the upward direction. The second portion is on a proximal side of the first portion and can bend in the upward direction and in right and left directions along a circumferential direction of the upward direction. The first distal side-traction member is fixed to a position of the second portion, separated from the upward direction toward the right. The second distal side-traction member is fixed to a position of the second portion, separated from the upward direction toward the left direction. The proximal side-traction member pulls the first and second distal side-traction members in conjunction with the first bending drive mechanism.

11 Claims, 7 Drawing Sheets

(51) Int. Cl.
*G02B 23/24* (2006.01)
*A61M 25/01* (2006.01)
*A61B 1/04* (2006.01)

(52) U.S. Cl.
CPC ............ *G02B23/24* (2013.01); *G02B 23/2476* (2013.01); *A61M 25/0138* (2013.01); *A61M 25/0147* (2013.01); *A61M 2025/0161* (2013.01)

(56) References Cited

U.S. PATENT DOCUMENTS

| | | | |
|---|---|---|---|
| 8,137,308 B2* | 3/2012 | Schultz | 604/95.04 |
| 2009/0240110 A1* | 9/2009 | Miyawaki et al. | 600/149 |
| 2011/0295069 A1* | 12/2011 | Ouchi | 600/146 |
| 2013/0190567 A1 | 7/2013 | Miyoshi et al. | |

FOREIGN PATENT DOCUMENTS

| | | |
|---|---|---|
| JP | A-2003-220022 | 8/2003 |
| JP | 2004154177 A | 6/2004 |
| JP | A-2009-160211 | 7/2009 |
| JP | A-2009-279405 | 12/2009 |
| JP | A-2010-201 | 1/2010 |
| JP | A-2012-196269 | 10/2012 |
| WO | WO 2011/111266 A1 | 9/2011 |
| WO | WO 2011/145681 A1 | 11/2011 |
| WO | 2013/008821 A1 | 1/2013 |

OTHER PUBLICATIONS

Jan. 28, 2014 Office Action issued in Japanese Patent Application No. 2013-555682 (with translation).

Oct. 14, 2014 International Search Report on Patentability issued in International Application No. PCT/JP2013/060492.

Aug. 25, 2015 Office Action issued in Chinese Patent Application No. 201380005449.0.

Feb. 16, 2016 European Supplementary Search Report issued in European Patent Application No. 13775060.0.

\* cited by examiner

ENDOSCOPE

CROSS-REFERENCE TO RELATED APPLICATIONS

This is a Continuation Application of PCT Application No. PCT/JP2013/060492, filed Apr. 5, 2013, which was published under PCT Article 21(2) in Japanese.

This application is based upon and claims the benefit of priority from the prior Japanese Patent Application No. 2012-090894, filed Apr. 12, 2012, the entire contents of which are incorporated herein by reference.

BACKGROUND OF THE INVENTION

1. Field of the Invention

The present invention relates to an endoscope including a plurality of bending portions.

2. Description of the Related Art

For example, Jpn. Pat. Appln. KOKAI Publication No. 2010-201 discloses a structure such that, when a first bending portion reaches a predetermined bending angle, a second bending portion is caused to bend in conjunction with the first bending portion. In this endoscope, when the first bending portion is caused to bend in, e.g., a U-direction with an angle exceeding 180°, the second bending portion bends in an R-direction.

BRIEF SUMMARY OF THE INVENTION

According to one embodiment of the present invention, an endoscope includes: an insertion section including a first bending portion and a second bending portion provided on a proximal end side of the first bending portion; a first bending drive mechanism including a first traction member passing inside the second bending portion and configured to bend the first bending portion to bend, and an operation input portion configured to receive an operation input so as to bend the first bending portion; and a second bending drive mechanism configured to act in response to an operation input to the operation input portion, and including at least one set of second traction members separated from the first traction member by distances almost equal to each other in a circumferential direction of the second bending portion to apply a compressive force to the second bending portion when being pulled.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will now be described with reference to the accompanying drawings.

An explanation will be given of a first embodiment with reference to FIGS. 1A to 3.

Figure 1A:
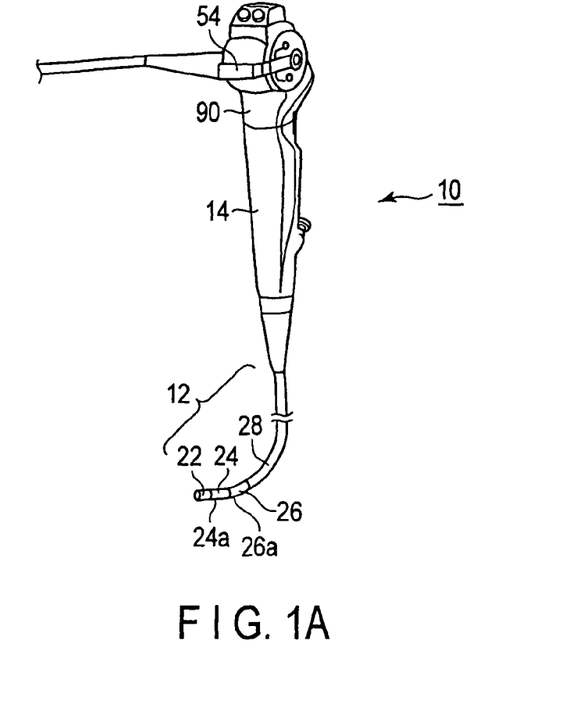
FIG. 1A is a schematic view showing an endoscope according to first to third embodiments.

As shown in FIG. 1A, an endoscope 10 includes a long and thin insertion section 12 and an operation section 14 provided at the proximal end portion of the insertion section 12. Inside the endoscope 10, an observation optical system and an illumination optical system (both of which are not shown) are disposed as in general endoscopes. The endoscope 10 preferably includes channels (not shown) formed therein to feed air, to feed water, and to insert a treatment device.

The insertion section 12 includes a distal end hard portion 22, a first bending portion 24, a second bending portion 26, and a flexible tube portion (tubular portion) 28 in this order from the distal end side toward the proximal end side. The proximal end of the flexible tube portion 28 is coupled to the operation section 14.

As described later, the first bending portion 24 serves as a so-called active bending portion, which is caused to bend by operating the operation section 14. The second bending portion 26 serves as a so-called passive bending portion when the bending angle of the first bending portion 24 is small (i.e., the bending amount is small). As the bending angle (or bending amount) of the first bending portion 24 is increased, the second bending portion 26 becomes easier to bend in the same direction as the bending direction of the first bending portion 24 and becomes more difficult to bend in the opposite direction. Further, the second bending portion 26 can be set to be actively caused to bend.

Figure 1B:
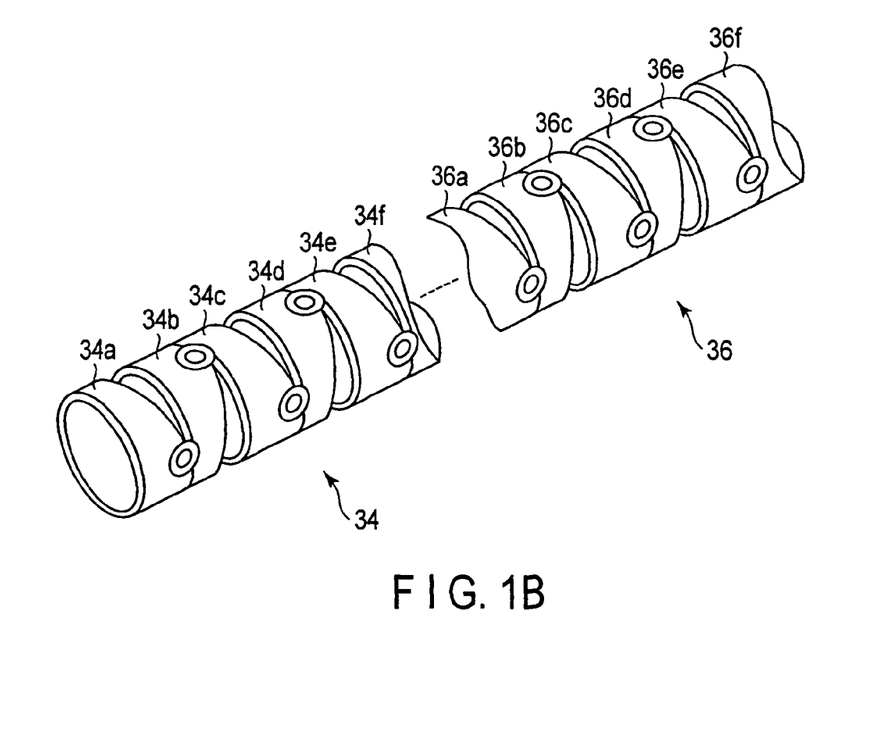
FIG. 1B is a perspective view schematically showing part of a bending tube used for a first bending portion and a second bending portion in the insertion section of the endoscope according to the first to third embodiments.

The first bending portion 24 shown in FIG. 1A includes a first bending tube 34 in which a plurality of bending pieces 34a, 34b, and so forth are arrayed side by side in the axial direction, as shown in FIG. 1B. The first bending tube 34 supports first angle wires 60a and 60b described later to be movable in the axial direction by use of wire guides (not shown) formed in the respective bending pieces 34a, 34b, and so forth. The distal ends of the first angle wires 60a and 60b are fixed, for example, to the distal endmost bending piece 34a of the first bending tube 34 or the distal end hard portion 22.

The second bending portion 26 includes a second bending tube 36 in which a plurality of bending pieces 36a, 36b, and so forth are arrayed side by side in the axial direction, the second bending tube 36 is structured in the same manner as the bending tube 34 of the first bending portion 24. The second bending tube 36 supports distal end side traction members 80a, 80b, 80c, and 80d described later to be movable in the axial direction by use of wire guides (not shown) formed in the respective bending pieces 36a, 36b, and so forth. The distal ends of the distal end side traction members 80a, 80b, 80c, and 80d are fixed, for example, to the distal endmost bending piece 36a of the second bending tube 36 or the proximal endmost bending piece of the first bending tube 34.

The first bending tube 34 of the first bending portion 24 and the second bending tube 36 of the second bending portion 26 can bend relative to the common central axis C. In this embodiment, each of them can bend in four directions relative to the straight state (the bending angle is 0° (zero degrees)), wherein the four directions are an upward direction (U-direction), a downward direction (D-direction), a right direction (R-direction), and a left direction (L-direction). The lengths of the first and second bending tubes 34 and 36 can be respectively and appropriately set.

In this embodiment, each of the bending tube 34 of the first bending portion 24 and the bending tube 36 of the second bending portion 26 can bend in the four directions, but, for the sake of simplified explanation, it is assumed that the first bending portion 24 can be operated to bend only in two directions of the upward direction and the downward direction.

The first bending portion 24 and the second bending portion 26 are structured, for example, such that braid (not shown) are disposed outside the first bending tube 34 and the second bending tube 36, and outer tubes 24a and 26a, which are made of, e.g., a rubber material and thus are elastic, are disposed outside the braids.

Figure 2A:
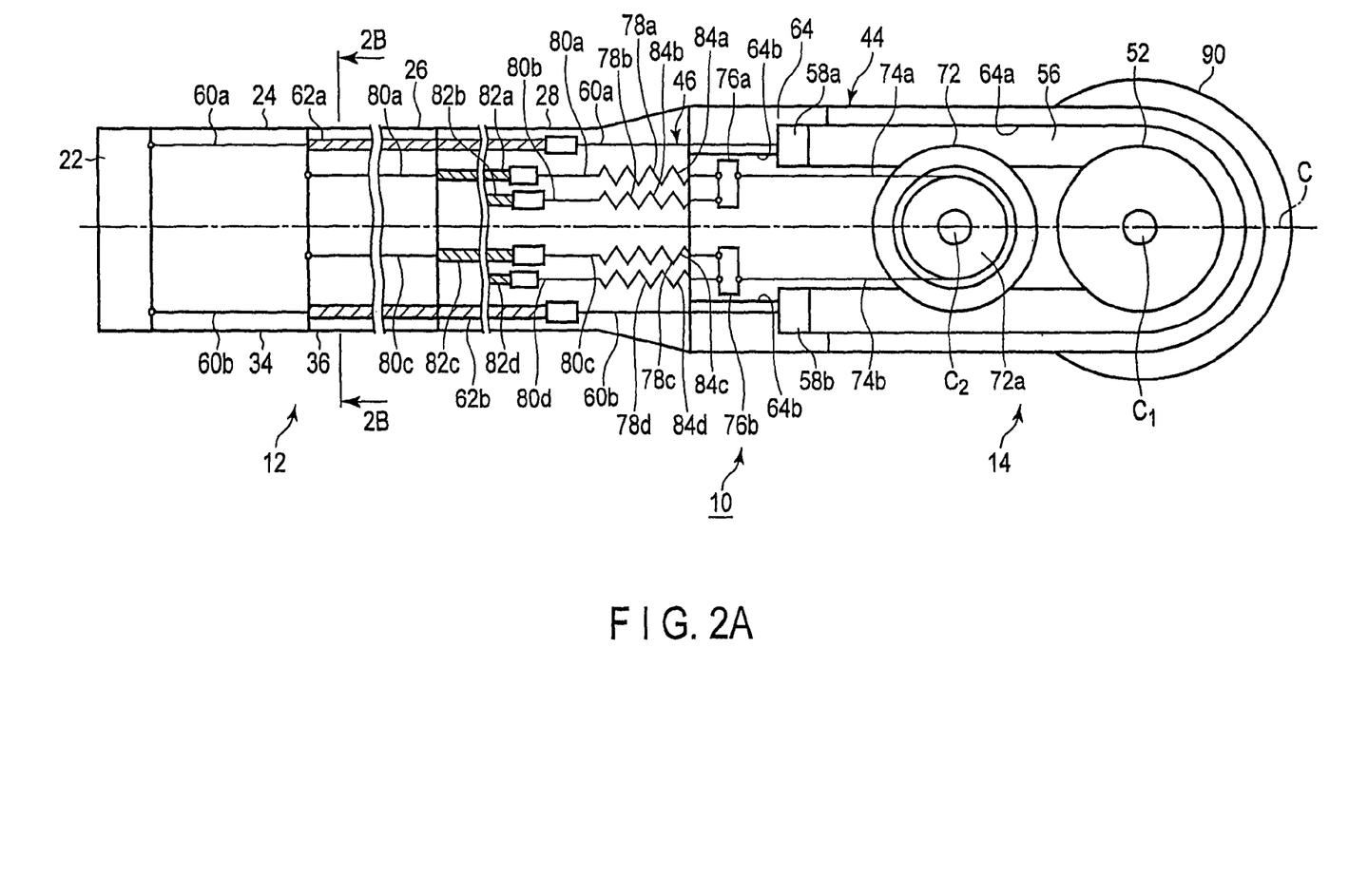
FIG. 2A is a longitudinal sectional view taken along a line 2A-2A in FIG. 2B and schematically showing the inner structure of the insertion section and operation section of the endoscope, in a state where the first bending portion and the second bending portion are straight according to the first embodiment.
Figure 2B:
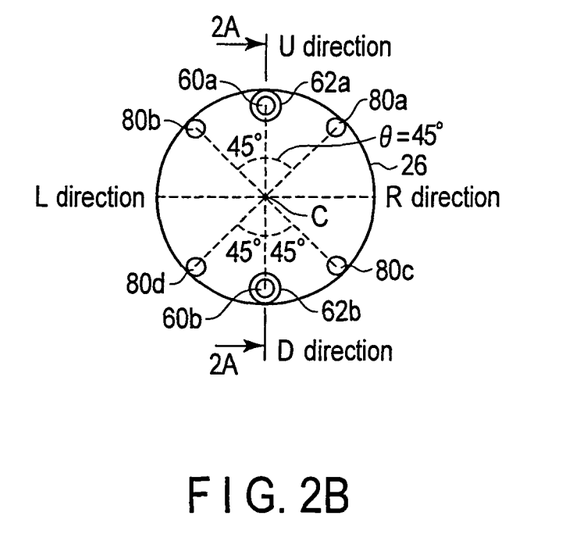
FIG. 2B is a schematically transverse sectional view taken along a line 2B-2B in FIG. 2A.

As shown in FIGS. 2A and 2B, the endoscope 10 includes a first bending drive mechanism 44 configured to cause the first bending portion 24 to bend in a plurality of directions, and a second bending drive mechanism 46 configured to follow driving of the first bending drive mechanism 44 so as to cause the second bending portion 26 to maintain the straight state or to cause the second bending portion 26 to bend in the same direction as the bending direction of the first bending portion 24. In other words, the first bending drive mechanism 44 and the second bending drive mechanism 46 are provided on the insertion section 12 and the operation section 14.

The first bending drive mechanism 44 includes a first sprocket (chain drum) 52 disposed inside the operation section 14, a first bending portion operation knob (bending operation input portion) 54, a chain 56 wound around and meshing with the first sprocket 52, first connection members (first traction members) 58a and 58b provided at the respective ends of the chain 56, first angle wires (first traction members) 60a and 60b, and first coil pipes 62a and 62b in which the first angle wires 60a and 60b are inserted.

The operation section 14 includes a base plate 64 disposed inside the operation section 14. For example, the base plate 64 preferably has dimensions such that its length in a direction along the axial direction of the insertion section 12 is larger than its length in a direction orthogonal to the axial direction of the insertion section 12.

The first sprocket 52 is supported by the base plate 64 to be rotatable about the central axis C1 of the first sprocket 52. The first bending portion operation knob 54 is disposed outside of the operation section 14 and configured to rotate the first sprocket 52 about its central axis C1. Thus, the first sprocket 52 and the first bending portion operation knob 54 move integrally with each other relative to the operation section 14. Accordingly, the operation amount of the first bending portion operation knob 54 is reflected in the movement amount of the first sprocket 52, i.e., in the rotation amount. For example, a chain guide 64a is formed on the base plate 64 to move the chain 56 in a predetermined direction when the first sprocket 52 is rotated about its central axis C1. The base plate 64 helps the chain 56 keep meshing with the first sprocket 52 and a second sprocket 72 described later.

The distal ends of the first angle wires 60a and 60b are fixed to the proximal end of the distal end hard portion 22 and to the distal end of the first bending tube 34 of the first bending portion 24. The proximal ends of the first angle wires 60a and 60b are supported by the first connection members 58a and 58b. The distal ends of the first coil pipes 62a and 62b are fixed at the proximal end of the bending tube 34 of the first bending portion 24 and at positions of the distal end of the bending tube 36 of the second bending portion 26. The proximal ends of the first coil pipes 62a and 62b are supported in, for example, near the boundary between the proximal end portion of the insertion section 12 and the operation section 14. The proximal ends of the first coil pipes 62a and 62b are preferably fixed to the base plate 64.

As described above, the endoscope 10 according to this embodiment has a structure (as a bending mechanism for the first bending portion 24) that can cause the first bending portion 24 to bend from the straight state in the U-direction and D-direction, which are opposite to each other, wherein this structure is the same as a structure (bending mechanism) used in general endoscopes.

The maximum bending angle of the first bending portion 24 can be appropriately set, for example, to be 180° to 215° in each of the U-direction and D-direction.

The second bending drive mechanism 46 has a structure to interlock with the first bending drive mechanism 44. According to this structure, even if the first bending portion 24 is in the straight state, the second bending portion 26 is caused to passively bend in a plurality of directions in response to external forces applied to the second bending portion 26. Further, when the bending angle of the first bending portion 24 is increased from the straight state, a compressive force is generated on that side of the second bending portion 26 which faces the bending direction of the first bending portion 24, relative to the central axis C of the second bending tube 36.

The second bending drive mechanism 46 is disposed inside the operation section 14 and includes a second sprocket (chain drum) 72 including a drum 72a integrally formed therewith, proximal end side traction members (second traction members) 74a and 74b extending from the drum 72a, first and second support portions (second traction members) 76a and 76b respectively provided at the distal ends of the proximal end side traction members 74a and 74b, U-direction side buffer portions (second traction members) 78a and 78b supported by the first support portion 76a, D-direction side buffer portions (second traction members) 78c and 78d supported by the second support portion 76b, distal end side traction members (second traction members) 80a and 80b respectively provided at the distal ends of the U-direction side buffer portions 78a and 78b, distal end side traction members (second traction members) 80c and 80d respectively provided at the distal ends of the D-direction side buffer portions 78c and 78d, and coil pipes 82a, 82b, 82c, and 82d in which the distal end side traction members 80a, 80b, 80c, and 80d are inserted. Specifically, the U-direction side buffer portions 78a and 78b are disposed between the U-direction side support portion 76a and the distal end side traction members 80a and 80b. The D-direction side buffer portions 78c and 78d are disposed between the D-direction side support portion 76b and the distal end side traction members (second traction members) 80c and 80d. The base plate 64 includes a guide portion 64b formed thereon other than the chain guide 64a. Within the range of this guide portion 64b, the proximal end side traction members 74a and 74b, the support portions 76a and 76b, and the buffer portions 78a, 78b, 78c, and 78d are movable in a predetermined direction (axial direction).

The second sprocket 72 may be supported to be rotatable about its central axis C2 by the base plate 64 disposed inside the operation section 14, for example, it may be supported to be rotatable about its central axis C2 by an extending portion (not shown) extending from the first sprocket 52, or it may be supported by both of them. The chain 56 meshing with the first sprocket 52 also meshes with the second sprocket 72. Thus, when the first bending portion operation knob 54 is rotated about its central axis C1, not only the first sprocket 52 is rotated, but also the second sprocket 72 is rotated about its central axis C2 in the same direction as the first sprocket 52. In other words, the second bending drive mechanism 46 is driven in conjunction with the first bending drive mechanism 44.

The axis of the drum 72a and the axis of the second sprocket 72 are on the same axis (central axis C2), and the diameter of the drum 72a is smaller than the diameter of the second sprocket 72. Consequently, the chain 56 is prevented from interfering with the proximal end side traction members 74a and 74b, the support portions 76a and 76b, and the buffer portions 78a, 78b, 78c, and 78d, so that the outer shell of the operation section 14 does not need to be enlarged.

The buffer portions 78a, 78b, 78c, and 78d include elastic members 84a, 84b, 84c, and 84d each formed of, e.g., an elastic coil spring or an elastic rubber material. In this embodiment, each of the elastic members 84a, 84b, 84c, and 84d is formed of one coil spring. Each of the buffer portions 78a, 78b, 78c, and 78d is not limited to be formed of a single one of the elastic members 84a, 84b, 84c, and 84d, but may be formed of a plurality of elastic members.

The elastic members 84a, 84b, 84c, and 84d of the buffer portions 78a, 78b, 78c, and 78d will be described later, although they have been adjusted such that, when the first bending portion 24 is caused to bend, they generate a force amount that makes the second bending portion 26 difficult to bend in the opposite direction to the bending direction of the first bending portion 24. For example, the elastic members 84a, 84b, 84c, and 84d of the buffer portions 78a, 78b, 78c, and 78d are adjusted as follows. Specifically, it is assumed that the second bending portion 26 is set in the straight state and the second bending portion 26 does not receive any external force applied thereto. In this state, when the first bending portion 24 is caused to bend at the maximum, the second bending portion 26 does not bend in the same direction as the bending direction of the first bending portion 24 but maintains the straight state. Further, when the second bending portion 26 receives a force applied thereto in a different direction, such as in the opposite direction to the bending direction of the first bending portion 24, the second bending portion 26 is prevented from bending in the different direction, such as the opposite direction. The adjustment of the elastic members 84a, 84b, 84c, and 84d may be performed preferably along with, e.g., adjustment of the lengths of the distal end side traction members 80a, 80b, 80c, and 80d.

The initial lengths of the elastic members (coil springs) 84a, 84b, 84c, and 84d of the buffer portions 78a, 78b, 78c, and 78d slightly vary depending on the orientation of the endoscope 10 and particularly on the orientation of the operation section 14. When the insertion section 12 and the operation section 14 are laterally orientated, the elastic members 84a, 84b, 84c, and 84d of the buffer portions 78a, 78b, 78c, and 78d are, for example, their natural length. When they are longitudinally orientated (in the vertical direction), the elastic members 84a, 84b, 84c, and 84d of the buffer portions 78a, 78b, 78c, and 78d come into an extended state due to the weight of the elastic members 84a, 84b, 84c, and 84d and the weight of the distal end side traction members 80a, 80b, 80c, and 80d. In this specification, the straight state of the second bending portion 26 is called a "neutral state", without reference to the stretch of the elastic members 84a, 84b, 84c, and 84d.

The distal ends of the distal end side traction members 80a, 80b, 80c, and 80d are at the proximal end of the bending tube 34 of the first bending portion 24 and are fixed to the distal end of the second bending tube 36 of the second bending portion 26. The proximal ends of the distal end side traction members 80a, 80b, 80c, and 80d are fixed to the buffer portions 78a, 78b, 78c, and 78d. Specifically, the distal end side traction members 80a, 80b, 80c, and 80d are coupled at their one-side ends to the second bending portion 26 and are extended toward the proximal end portion of the insertion section 12. The distal ends of the coil pipes 82a, 82b, 82c, and 82d are fixed at the proximal end of the bending tube 36 of the second bending portion 26 and at positions corresponding to the distal end of the flexible tube portion 28. The proximal ends of the coil pipes 82a, 82b, 82c, and 82d are supported, for example, near the boundary between the proximal end portion of the insertion section 12 and the operation section 14. The proximal ends of the coil pipes 82a, 82b, 82c, and 82d are preferably fixed to the base plate 64.

The tensile force applied to the proximal end side traction members 74a and 74b and the distal end side traction members 80a, 80b, 80c, and 80d is smaller than the tensile force applied to the first angle wires 60a and 60b, and so the proximal end side traction members 74a and 74b and the distal end side traction members 80a, 80b, 80c, and 80d can be thinner than the first angle wires 60a and 60b. Further, the coil pipes 82a, 82b, 82c, and 82d can be thinner than the coil pipes 62a and 62b.

As shown in FIG. 2B, inside the first and second bending portions 24 and 26 of the insertion section 12 and inside the flexible tube portion 28, the coil pipe 62a in which the angle wire 60a is inserted on the U-direction side and the coil pipe 62b in which the angle wire 60b is inserted on the D-direction side are at positions to face each other with the central axis C interposed therebetween. Thus, if it is defined that the angle wire 60a and the coil pipe 62a on the U-direction side are positioned at 0° relative to the central axis C, the angle wire 60b and the coil pipe 62b on the D-direction side are positioned at almost 180°.

Further, according to this definition that the angle wire 60a and the coil pipe 62a on the U-direction side are positioned at 0° relative to the central axis C, the distal end side traction member 80a, which is one of the pair of distal end side traction members 80a and 80b, is preferably positioned at an angle θ of almost +45°. In this case, the distal end side traction member 80b, which is the other of the pair of distal end side traction members 80a and 80b, is positioned at an angle θ of almost −45° (almost +315°).

Further, according to this definition that the angle wire 60a and the coil pipe 62a on the U-direction side are positioned at 0° relative to the central axis C, the distal end side traction member 80c, which is one of the pair of distal end side traction members 80c and 80d, is preferably positioned at an angle θ of almost +135°. In this case, the distal end side traction member 80d, which is the other of the pair of distal end side traction members 80c and 80d, is preferably positioned at an angle θ of almost +225°.

Accordingly, the U-direction side angle wire 60a and the distal end side traction members 80a and 80b on the U-direction side have a relationship such that the central angles θ relative to the central axis C of the second bending portion 26 are smaller than 90° and almost equal to each other (almost equidistant). In other words, relative to the angle wire 60a and the coil pipe 62a on the U-direction side, the pair of distal end side traction members 80a and 80b are separately disposed with distances almost equal to each other in the circumferential direction of the second bending portion 26. More specifically, the distal end side traction members 80a and 80b are preferably positioned relative to the U-direction side angle wire 60a such that each of them forms a central angle θ of almost 45°, which allows for a deviation within a range of, e.g., from several degrees to ten and several degrees. Further, the D-direction side angle wire 60b and the distal end side traction members 80c and 80d on the D-direction side have a relationship such that the central angles θ relative to the central axis C of the second bending portion 26 are smaller than 90° and almost equal to each other (almost equidistant). In other words, relative to the angle wire 60b and the coil pipe 62b on the D-direction side, the pair of distal end side traction members 80c and 80d are separately disposed with distances almost equal to each other in the circumferential direction of the second bending portion 26. More specifically, the distal end side traction members 80c and 80d are preferably positioned relative to the D-direction side angle wire 60b such that each of them forms a central angle θ of almost 45°, which allows for a deviation within a range of, e.g., from several degrees to ten and several degrees.

In a case where the central angle θ is almost 45°, although this will be described later, when the first bending portion 24 is caused to bend in, e.g., the U-direction, a compressive force component in the U-direction and compressive force components in the R-direction and L-direction can be exerted. Further, when the first bending portion 24 is caused to bend in, e.g., the D-direction, a compressive force component in the D-direction and compressive force components in the R-direction and L-direction can be exerted. More specifically, when the first bending portion 24 is caused to bend in, e.g., the U-direction, it is possible to apply a force for preventing the second bending portion 26 from falling in the D-direction and further to exert a force for preventing the second bending portion 26 from falling in the R-direction and L-direction. Further, when the first bending portion 24 is caused to bend in, e.g., the D-direction, it is possible to apply a force for preventing the second bending portion 26 from falling in the U-direction and further to exert a force for preventing the second bending portion 26 from falling in the R-direction and L-direction. Consequently, when the first bending portion 24 is caused to bend to either one of the U-direction side and D-direction side, it is possible to prevent the second bending portion 26 from bending in the R-direction and L-direction.

The central angle θ is not limited to 45°, and, for example, the central angle θ is permitted to be within a range of about from 30° to 60°. By adjusting the central angle θ, it is possible to appropriately set a force for preventing the second bending portion 26 from falling in the U-direction or D-direction and a force for preventing the second bending portion 26 from falling in the R-direction or L-direction. Thus, by use of adjustment of the central angle θ, when the first bending portion 24 is caused to bend in, e.g., the U-direction, a compressive force component in the U-direction and compressive force components in the R-direction and L-direction can be respectively exerted with adequate levels. Further, when the first bending portion 24 is caused to bend in, e.g., the D-direction, a compressive force component in the D-direction and compressive force components in the R-direction and L-direction can be respectively exerted with adequate levels.

The operation section 14 includes a cover 90. The cover 90 is supported by the base plate 64, while the cover 90 covers the first sprocket 52, the second sprocket 72, the chain 56, the first connection members 58a and 58b, the first angle wires 60a and 60b, the proximal end side traction members 74a and 74b, the support portions 76a and 76b, and the buffer portions 78a, 78b, 78c, and 78d, which are disposed on the base plate 64, and the cover 90 forms a gripping portion for a user of the endoscope 10 to grip thereof by, e.g., the left hand. The cover 90 may be formed to further cover the proximal ends of the distal end side traction members 80a, 80b, 80c, and 80d. The first bending portion operation knob 54 is present outside the cover 90 to be operable by, e.g., the left hand.

Next, an explanation will be given of functions of the endoscope 10 according to this embodiment.

Figure 3:
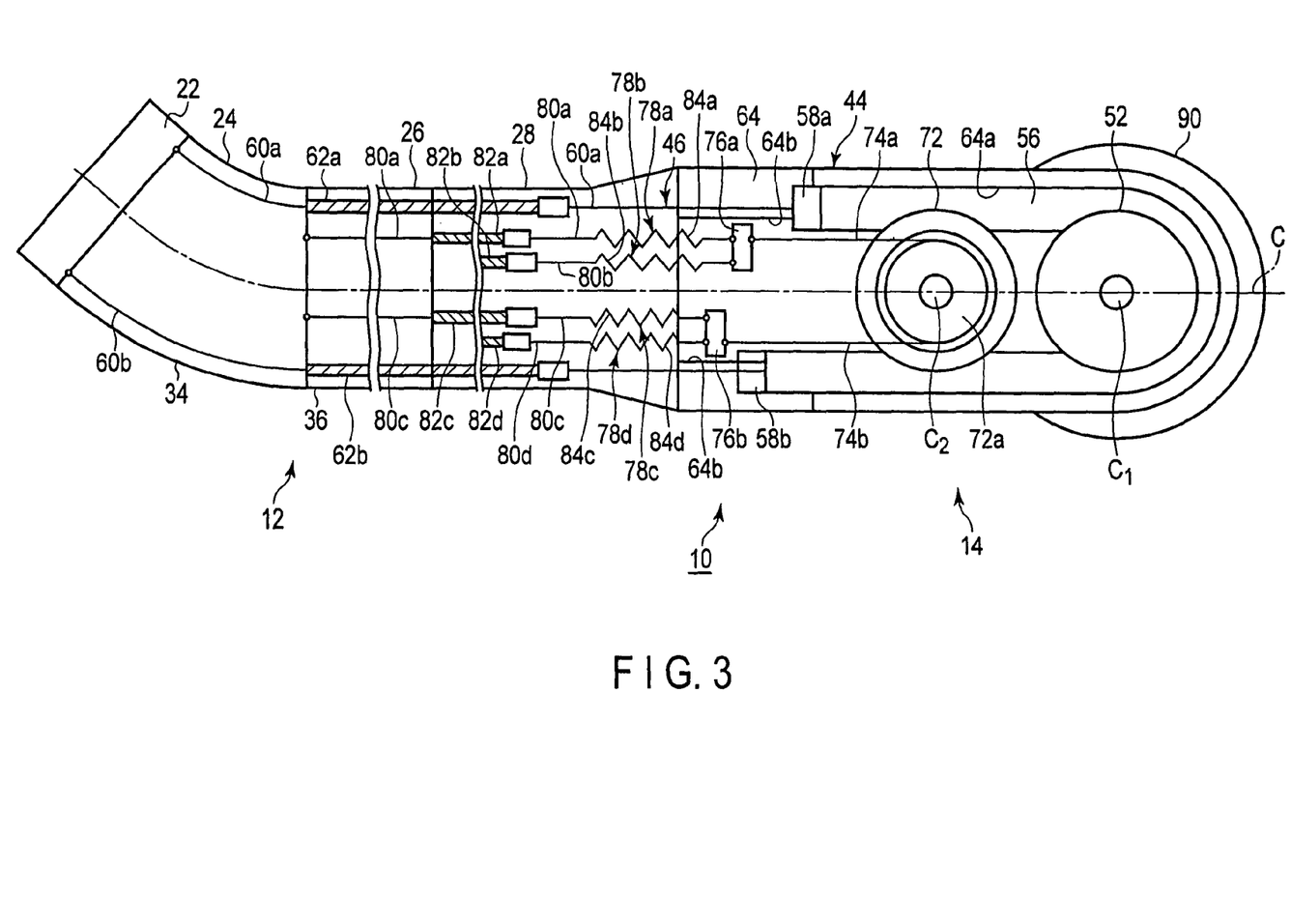
FIG. 3 is a longitudinal sectional view schematically showing the inner structure of the insertion section and operation section of the endoscope, in a state where the first bending portion and the second bending portion start being caused to bend in a U-direction, according to the first embodiment.

For example, from a state where the first bending portion 24 and the second bending portion 26 are straight, the first bending portion operation knob 54 is rotated for the first bending portion 24 to bend in the U-direction. When the first sprocket 52 is rotated by the rotation of the first bending portion operation knob 54, the wire 60a, which is one of the first angle wires 60a and 60b, is pulled through the chain 56 and the first connection members 58a and 58b. The distal end of the wire 60a is fixed to the bending piece 34a or the distal end hard portion 22. Accordingly, when the wire 60a is pulled, the U-direction side of the bending piece 34a is pulled to the proximal end side, and the bending pieces 34a, 34b, and so forth are sequentially turned to cause the first bending tube 34 to bend to the U-direction side. Consequently, the first bending portion 24 bends in the U-direction.

When the first sprocket 52 is rotated by the rotation of the first bending portion operation knob 54, the second sprocket 72 is simultaneously rotated by the chain 56 in the same direction as the rotational direction of the first sprocket 52, and so the drum 72a coaxial with the second sprocket 72 (on the central axis C2) is integrally rotated. Consequently, the proximal end side traction member 74a, which is one of the proximal end side traction members 74a and 74b, is pulled, and the support portion 76a, which is one of the support portions 76a and 76b, is thereby pulled. As a result, the elastic members 84a and 84b of the buffer portion 78a, which is one of the buffer portions 78a and 78b, are extended, for example, from a state where they are their natural length or a state where they are stretched due to their own weight and so forth, i.e., from the neutral state.

The proximal end side traction member 74b, the support portion 76b, the elastic members 84c and 84d of the buffer portions 78c and 78d, and the distal end side traction members 80c and 80d, which are in the other group, are about to move to the distal end side of the insertion section 12, but they cause a deflection due to the flexibility of the proximal end side traction member 74b and that of the distal end side traction members 80c and 80d.

When the elastic members 84a and 84b of the buffer portions 78a and 78b start being extended, the extension amount of the elastic members 84a and 84b is very small, and so the tensile force to the distal end side traction members 80a and 80b is weak. As the elastic members 84a and 84b of the buffer portions 78a and 78b are being extended, the elastic members 84a and 84b of the buffer portions 78a and 78b increase the tensile force to pull the distal end side traction members 80a and 80b toward the proximal end side traction member 74a. Consequently, a tension is applied to the distal end side traction members 80a and 80b.

In this case, the elastic members 84a and 84b of the buffer portions 78a and 78b are present between the proximal end side traction member 74a and the distal end side traction members 80a and 80b. Accordingly, the tensile force generated at this time becomes smaller than that which would be generated in a case where the distal end side traction members 80a and 80b are directly wound around the drum 72a and the distal end side traction members 80a and 80b are thereby pulled.

As described above, when the elastic members 84a and 84b of the buffer portions 78a and 78b are pulled by the proximal end side traction member 74a, the tensile force to the distal end side traction members 80a and 80b is weak at the beginning of extension of the elastic members 84a and 84b. Then, as the elastic members 84a and 84b of the buffer portions 78a and 78b are being extended, the tensile force to the distal end side traction members 80a and 80b is gradually increased, so that the buffer portions 78a and 78b exert a buffer function.

Then, when the bending angle (bending amount) of the first bending portion 24 increases in the U-direction from the straight state (initial state), the second bending portion 26 serves as a passive bending portion that is caused to passively bend in response to an external force, because in the initial state hardly any tensile force is applied to the distal end side traction members 80a, 80b, 80c, and 80d of the second bending drive mechanism 46. As the bending angle (bending amount) of the first bending portion 24 increases, the tensile force applied to the distal end side traction members 80a and 80b is gradually increased. However, at this time, while the bending angle of the first bending portion 24 is small, the second bending portion 26 serves as a passive bending portion as in the initial state. Then, as the bending angle of the first bending portion 24 increases, the tensile force applied to the distal end side traction members 80a and 80b is further increased. Accordingly, in relation to the distal end side traction members 80a and 80b present between the distal end and proximal end of the bending tube 36 of the second bending portion 26, when the first bending portion 24 is caused to bend from the straight state, they do not immediately receive a force applied thereto. Then, as the bending amount of the first bending portion 24 increases, they come to receive a compressive force on their side facing the bending direction of the first bending portion 24, relative to the central axis C of the second bending tube 36 of the second bending portion 26.

In this embodiment, even if the maximum tensile force is applied to the distal end side traction members 80a and 80b when the first bending portion 24 is caused to bend, the compressive force loaded onto the second bending portion 26 is not sufficient to turn the bending pieces 36a, 36b, and so forth of the bending tube 36 of the second bending portion 26, i.e., the second bending portion 26 remains straight. In other words, in order to attain this state, the elastic members 84a and 84b of the buffer portions 78a and 78b are selected for use, the elastic members 84a and 84b of the buffer portions 78a and 78b are adjusted, and/or the lengths of the distal end side traction members 80a and 80b are adjusted.

Further, the elastic force of the exterior covering 26a made of, e.g., a rubber material and used for the bending tube 36 of the second bending portion 26, and/or the stretch of the distal end side traction members 80a and 80b can be utilized to assist the second bending portion 26 to maintain the straight state.

As described above, when the first bending portion 24 is, for example, in the maximum bending angle state, the area between the distal end and proximal end of the bending tube 36 of the second bending portion 26 is in a state where the distal end side traction members 80a and 80b on the U-direction side receive a compressive force applied thereto, while the distal end side traction members 80c and 80d on the D-direction side do not receive any force applied thereto. Accordingly, when the first bending portion 24 is, for example, in the maximum bending angle state and an external force is applied to the second bending portion 26, if a pressing force is loaded from the D-direction side, the second bending portion 26 can bend in the U-direction, because the distal end side traction members 80a and 80b have been prepared in advance to be easy to bend in the U-direction by a compressive force. When the second bending portion 26 bends in the same direction as the bending direction of the first bending portion 24, as described above, it is preferable that the second bending portion 26 bends with a bending angle smaller than the bending angle of the first bending portion 24. On the other hand, when a pressing force is loaded from the U-direction side, the second bending portion 26 exerts a resistance against bending in the D-direction to maintain the straight state due to a compressive force loaded onto the second bending portion 26.

Further, the bending pieces 36a, 36b, and so forth of the bending tube 36 of the second bending portion 26 are configured to bend not only in the U-direction and D-direction, but also in the R-direction and L-direction by an external force, i.e., they can bend in the four directions. The distal end side traction members 80a and 80b on the U-direction side are disposed at positions of almost ±45° relative to the U-direction side angle wire 60a. Thus, the distal end side traction members 80a and 80b on the U-direction side generate a compressive force at positions with a central angle θ of almost ±45° relative to the U-direction side angle wire 60a. Accordingly, when an external force is applied, for example, from the R-direction side of the second bending portion 26, the second bending portion 26 is prevented from bending in the R-direction, because a compressive force has been applied to the distal end side traction members 80a and 80b on the U-direction side. When an external force is applied, for example, from the L-direction side of the second bending portion 26, the second bending portion 26 is prevented from bending in the L-direction, because a compressive force has been applied to the distal end side traction members 80a and 80b on the U-direction side. Further, when an external force is applied, for example, from the R-direction side of the first bending portion 24, the second bending portion 26 is prevented from bending in the L-direction, because a compressive force has been applied to the distal end side traction members 80a and 80b on the U-direction side. Furthermore, when an external force is applied, for example, from the L-direction side of the first bending portion 24, the second bending portion 26 is prevented from bending in the R-direction, because a compressive force has been applied to the distal end side traction members 80a and 80b on the U-direction side. Accordingly, it is possible to prevent the second bending portion 26 from falling in the R-direction and L-direction, i.e., from causing so-called sinking, and further to make the second bending portion 26 easy to bend in the same direction as the bending direction of the first bending portion 24 and difficult to bend in the opposite direction.

After the first bending portion 24 is caused to bend, for example, with the maximum bending amount, when the first bending portion operation knob 54 is operated to return the first bending portion 24 to the straight state, the second sprocket 72 is rotated in the same direction as the first sprocket 52. Consequently, the proximal end side traction member 74a is moved toward the distal end side of the insertion section 12, and the lengths of the elastic members 84a and 84b of the buffer portions 78a and 78b are returned to the neutral state. Accordingly, when the bending angle of the first bending portion 24 becomes smaller, the compressive force applied by the distal end side traction members 80a and 80b between the distal end and proximal end of the second bending portion 26 is cancelled.

In this embodiment, the insertion section 12 and the operation section 14 of the endoscope 10 are designed to be symmetric relative to the central axis C, and so no explanation will be given of a case where the first bending portion 24 is caused to bend in the D-direction.

As described above, the second bending portion 26 of the insertion section 12 in the endoscope 10 according to this embodiment serves as a passive bending portion when the first bending portion 24 is in the straight state or has a small bending angle. Then, as the bending angle of the first bending portion 24 increases, the second bending portion 26 serves as a passive bending portion that bends when it receives an external force in the same direction as the bending direction of the first bending portion 24, and also exerts a resistance not to bend or a resistance difficult to bend when it receives an external force in a different direction, such as the opposite direction to the bending direction of the first bending portion 24. Further, as the bending angle of the first bending portion 24 increases, and when the second bending portion 26 receives an external force from a direction of, e.g., almost 90° relative to the bending direction of the first bending portion 24, it exerts a resistance not to bend or a resistance difficult to bend in this direction. Accordingly, in accordance with the bending angle (bending amount) and bending direction of the first bending portion 24, the state of the second bending portion 26 automatically switches between a state in which it acts as a passive bending portion and a state in which it easily bends in the same direction as the first bending portion 24 and resists bending in the opposite direction.

Next, a brief explanation will be given of a case where the insertion section 12 of this endoscope 10 is inserted, for example, into a large intestine.

When an operator inserts the distal end of the insertion section 12 into a large intestine from the anus side, the operator firmly holds the insertion section 12 by the right hand, and performs an operation to feed the insertion section 12 to a deeper side of the large intestine and an operation to twist the insertion section 12, while controlling the endoscope 10 in consideration of a load to the large intestine by sensing a reaction force or the like from the large intestine.

When the distal end of the insertion section 12 comes to a curved portion of the large intestine, such as the sigmoid colon, the operator causes the first bending portion 24 to bend and thereby catch the curved portion from its nearer side to deeper side. While the first bending portion 24 is caused to bend in, e.g., the U-direction and thereby catch the curved portion from its nearer side to deeper side, the second bending portion 26 can bend in the U-direction by an external force, but the second bending portion 26 is prevented from bending in the D-direction.

Accordingly, the first and second bending portions 24 and 26 of the insertion section 12 can be used to reliably catch the curved portion from its nearer side to deeper side. At this time, when the second bending portion 26 bends from a state where the curved portion is held by the first bending portion 24, this state changes to a state where the curved portion is held by the first and second bending portions 24 and 26. Consequently, the distal end of the insertion section 12 is moved to a deeper side relative to the curved portion.

Further, when the first bending portion 24 is caused to largely bend, the second bending portion 26 is prevented from inclining in the R-direction and L-direction relative to the first bending portion 24. Accordingly, when the operator pushes the insertion section 12 to a deeper side along the large intestine, it is possible to push it along the large intestine with a smaller deviation in the circumferential direction.

Then, the operator returns the first bending portion 24 from the bending state to the straight state while feeding the distal end of the insertion section 12 toward a deeper side of the large intestine. Consequently, the distal end of the insertion section 12 is moved from the curved portion to a deeper side.

As described above, this embodiment can provide the following effects.

The second bending drive mechanism 46 interlocks with the first bending drive mechanism 44, and the second bending portion 26 can be caused to passively bend in a plurality of directions while the first bending portion 24 is in the straight state. Further, in this structure, when the bending angle of the first bending portion 24 is increased from the straight state, a compressive force is generated on that side of the second bending portion 26 which faces the bending direction of the first bending portion 24, relative to the central axis C of the second bending tube 36. Accordingly, when the first bending portion 24 is in the straight state or close to the straight state, the second bending drive mechanism 46 can cause the second bending portion 26 to freely and passively bend.

Then, when the bending angle of the first bending portion 24 is increased by the first bending drive mechanism 44, the second bending drive mechanism 46 acts in conjunction therewith, and the second bending drive mechanism 46 generates a compressive force to the second bending portion 26 on the same direction side as the bending direction of the first bending portion 24. Consequently, the second bending portion 26 is restricted from bending in the opposite direction to the bending direction of the first bending portion 24, and the second bending portion 26 is assisted to maintain the straight state or the second bending portion 26 is assisted to bend in the same direction as the bending direction of the first bending portion 24. Thus, when the first bending portion 24 is caused to bend in the U-direction, and the second bending portion 26 receives an external force, for example, from the U-direction side, the second bending portion 26 can resist this external force to prevent the second bending portion 26 from bending in the D-direction, so that the second bending portion 26 maintains the straight state or an almost straight state. Further, since a compressive force is applied to the U-direction side between the distal end and proximal end of the second bending portion 26, the second bending portion 26 easily bends on the U-direction side when the second bending portion 26 receives an external force, for example, from the D-direction side. Accordingly; in this embodiment, when the first bending portion 24 is caused to bend in, e.g., the U-direction, the second bending portion 26 is easily caused to bend in the U-direction and is prevented from bending in the D-direction.

For example, when the U-direction side angle wire 60a is pulled and the first bending portion 24 is thereby caused to bend, a compressive force is applied to a set of distal end side traction members 80a and 80b, which are separated from the U-direction side angle wire 60a by distances almost equal to each other in the circumferential direction of the second bending portion 26. More specifically, they are arranged such that, when the bending angle of the first bending portion 24 is increased, for example, in the U-direction by the first bending drive mechanism 44, a compressive force is applied to positions of almost ±45° relative to the U-direction side. Consequently, the second bending portion 26 is prevented from bending in the R-direction or L-direction by the compressive force applied to the set of distal end side traction members 80a and 80b, which are separated from the U-direction side angle wire 60a by distances almost equal to each other in the circumferential direction of the second bending portion 26. Thus, when an external force is applied to the first bending portion 24 or the second bending portion 26 from the R-direction or L-direction, it is possible to prevent the second bending portion 26 from falling in the R-direction and L-direction, i.e., from causing so-called sinking, and further to make the second bending portion 26 easy to bend in the same direction as the bending direction of the first bending portion 24 and difficult to bend in the opposite direction.

In addition, the angle wire 60a and the distal end side traction members 80a and 80b have a relationship such that the central angles θ relative to the central axis C of the second bending portion 26 are smaller than 90° and almost equal to each other. Further, the angle wire 60b and the distal end side traction members 80c and 80d have a relationship such that the central angles θ relative to the central axis C of the second bending portion 26 are smaller than 90° and almost equal to each other. Thus, the set of distal end side traction members 80a and 80b are present at positions close to the U-direction side angle wire 60a and distant from the D-direction side angle wire 60b. Further, the set of distal end side traction members 80c and 80d are present at positions close to the D-direction side angle wire 60b and distant from the U-direction side angle wire 60a. Accordingly, when the first bending portion 24 is caused to bend in, e.g., the U-direction, it is possible to exert a compressive force not only in the U-direction but also in the R-direction, i.e., in the UR-direction, and not only in the U-direction but also in the L-direction, i.e., in the UL-direction. Further, when the first bending portion is caused to bend in the D-direction, it is possible to exert a compressive force not only in the D-direction but also in the L-direction, i.e., in the DL-direction, and/or not only in the D-direction but also in the R-direction, i.e., in the DR-direction.

Particularly, by setting the central angle θ at 45°, when the first bending portion 24 is caused to bend in, e.g., the U-direction, the compressive force component in the U-direction and each of the compressive force component in the R-direction and L-direction on the second bending portion 26 can be almost the same as each other. Further, when the first bending portion 24 is caused to bend in, e.g., the D-direction, the compressive force component in the D-direction and each of the compressive force component in the R-direction and L-direction on the second bending portion 26 can be almost the same as each other.

Further, since the second bending drive mechanism 46 includes the buffer portions 78a, 78b, 78c, and 78d, it is possible to adjust (delay) the timing at which a compressive force is generated when a power is transmitted from the first bending drive mechanism 44 to the second bending drive mechanism 46. For example, since the elastic members 84a, 84b, 84c, and 84d, each of which is formed of, e.g., an elastic coil spring or an elastic rubber material, are used for the buffer portions 78a, 78b, 78c, and 78d, when the first bending portion 24 is caused to bend by the first bending drive mechanism 44, a compressive force can be generated with a desired timing on the same side of the second bending portion 26 as the bending side of the first bending portion 24 relative to the central axis C. Further, adjustment of the compressive force can be easily performed.

Further, since the U-direction side buffer portions 78a and 78b are present between the proximal end side traction member 74a and the distal end side traction members 80a and 80b, the buffer portions 78a and 78b can be disposed near the boundary between the insertion section 12 and the operation section 14, so that adjustment of the buffer portions 78a and 78b can be easily performed. This is also true for the D-direction side buffer portions 78c and 78d.

In this embodiment, an explanation has been given of a case where the support portion 76a, the buffer portions 78a and 78b, the distal end side traction members 80a and 80b, and the coil pipes 82a and 82b are disposed on the U-direction side, while the support portion 76b, the buffer portions 78c and 78d, the distal end side traction members 80c and 80d, and the coil pipes 82c and 82d are disposed on the D-direction side. However, it is also preferable that only the former group is disposed or only the latter group is disposed. For example, in a case where only the former group is disposed, for example, an expandable member that can easily expand and contract in the axial direction within a range larger than that of the buffer portions 78a, 78b, 78c, and 78d is used between the proximal end side traction member 74b and the distal endmost bending piece 36a of the second bending tube 36 or the proximal endmost bending piece of the first bending tube 34.

Next, an explanation will be given of a second embodiment with reference to FIGS. 4A to 4C. This embodiment is a modification of the first embodiment, wherein the same members and members having the same function as those explained in the first embodiment are denoted by the same reference numerals, and their detailed description will be omitted. Accordingly, the following explanation will be mainly given of variations of the first connection members 58a and 58b, the proximal ends of the first angle wires 60a and 60b, and the buffer portions 78a and 78b.

Figure 4A:
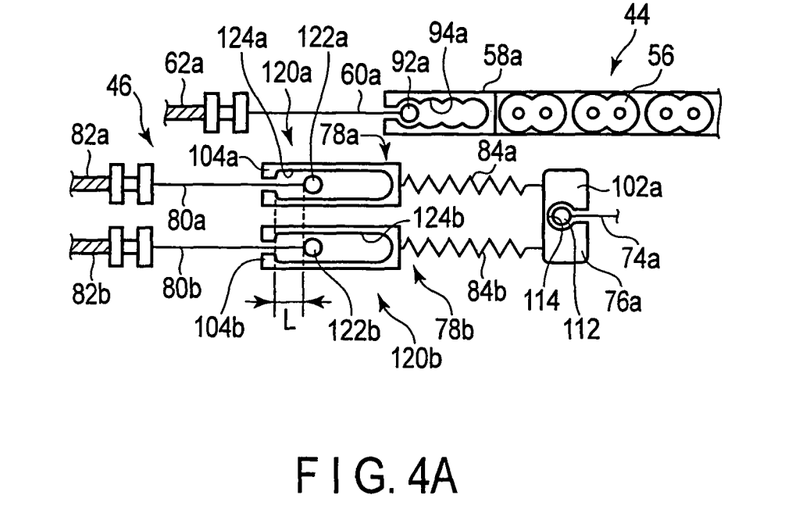
FIG. 4A is a view schematically showing the structure of a first bending drive mechanism and a second bending drive mechanism in the endoscope near the boundary between the insertion section and operation section, and shows a state where an engagement projection formed at the proximal end of an angle wire engages with an engagement recess formed in a connection member at an end of a chain, which interlocks with rotation of a first sprocket in the first bending drive mechanism, and further shows that sliders of distal end side traction members in the second bending drive mechanism are freely movable within slider receiving portions formed in distal end side coupling members, according to the second embodiment.

FIG. 4A partly shows the first bending drive mechanism 44 and the second bending drive mechanism 46 by their U-direction side mechanism part disposed near the boundary between the insertion section 12 and the operation section 14. FIG. 4A shows only the U-direction side, but the D-direction side preferably has the same structure.

As shown in FIG. 4A, engagement projections (engagement portions) 92a are respectively formed at the proximal ends of the first angle wires 60a and 60b. The first connection members 58a disposed at the respective ends of the chain 56 are respectively equipped with engagement recesses (engagement portions) 94a formed along the axial direction to respectively engage with the engagement projections 92a of the first angle wires 60a and 60b. Accordingly, by appropriately setting the position of each engagement projection 92a relative to the corresponding engagement recess 94a, it is possible to appropriately set the initial tension of the first angle wires 60a.

Figure 4B:
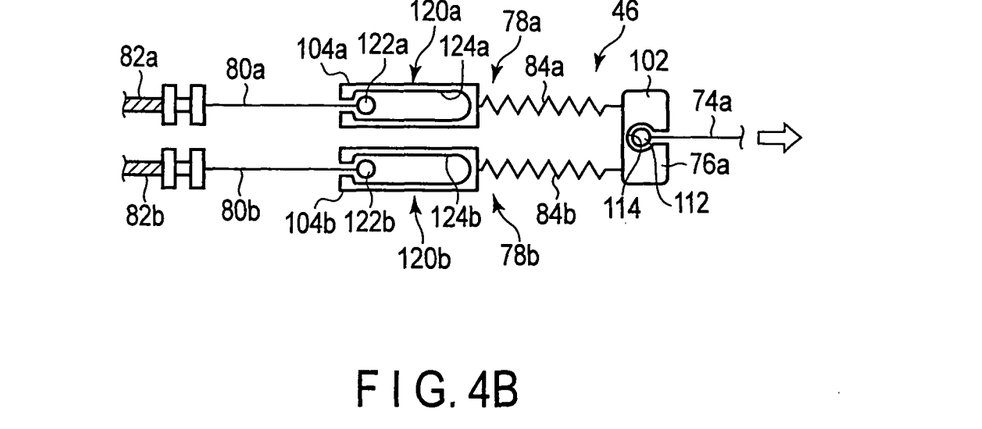
FIG. 4B is a view schematically showing the structure of the first bending drive mechanism and second bending drive mechanism of the endoscope near the boundary between the insertion section and operation section, and shows a state where a proximal end side traction member of the second bending drive mechanism is pulled and the distal end side coupling members are thereby moved, such that the sliders of the distal end side traction members come into contact with the distal ends of the slider receiving portions of the distal end side coupling members, according to the second embodiment.
Figure 4C:
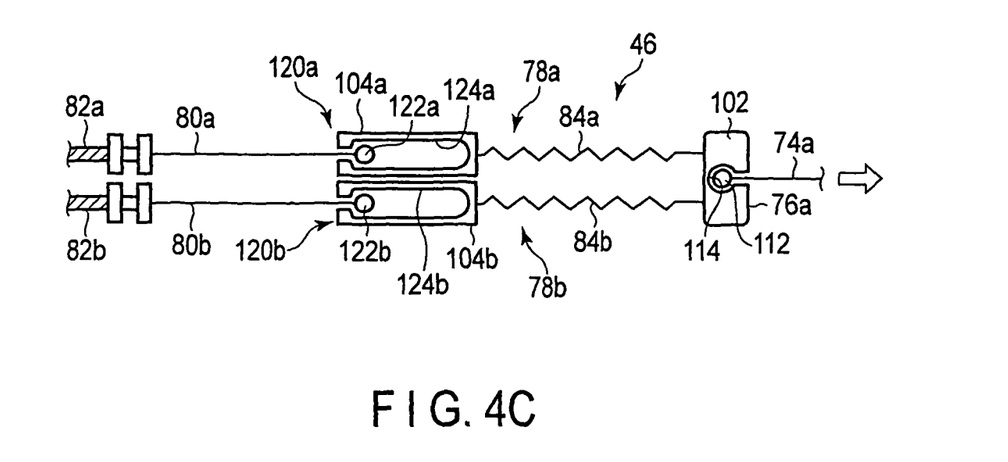
FIG. 4C is a view schematically showing the structure of the first bending drive mechanism and second bending drive mechanism of the endoscope near the boundary between the insertion section and operation section, and shows a state where the proximal end side traction member of the second bending drive mechanism is pulled further from the state shown in FIG. 4B to extend an elastic member and the distal end side coupling members are thereby moved, such that the sliders of the distal end side traction members are in contact with the distal ends of the slider receiving portions of the distal end side coupling members while the distal end side traction members are thereby pulled, according to the second embodiment.

As shown in FIGS. 4A to 4C, the U-direction side support portion 76a includes a proximal end side coupling member 102. The U-direction side buffer portion 78a includes an elastic member 84a formed of a coil spring or the like, as explained in the first embodiment, and a distal end side coupling member 104a. The elastic member 84a is disposed between the proximal end side coupling member 102 and the distal end side coupling member 104a. An engagement projection (engagement portion) 112 is formed at the distal end of the proximal end side traction member 74a. An engagement recess (engagement portion) 114 is formed in the proximal end side coupling member 102 of the support portion 76a. The engagement projection 112 engages with the engagement recess 114 and is supported so as not to come off during the normal action.

The buffer portion 78a cooperates with the proximal end of the distal end side traction member 80a to form a slider mechanism 120a. This slider mechanism 120a includes a slider 122a fixed to the proximal end of the distal end side traction member 80a, and a slider receiving portion (window portion) 124a formed in the distal end side coupling member 104a and configured to engage with the slider 122a slidably in the axial direction of the distal end side traction member 80a. In other words, the slider 122a is fixed to the proximal end of the distal end side traction member 80a. The distal end side coupling member 104a includes the slider receiving portion (window portion) 124a to engage with the slider 122a slidably in the axial direction of the distal end side traction member 80a.

Accordingly, the slider 122a can be relatively moved relative to the slider receiving portion 124a. The slider 122a is allowed to shift relative to the slider receiving portion 124a in the axial direction, and is restricted from shifting in a direction deviating from the axial direction, so that the slider 122a is supported so as not to come off from the slider receiving portion 124a during the normal action.

The slider 122a can be moved relative to the slider receiving portion 124a in the axial direction of the distal end side traction member 80a. When the elastic member 84a is, for example, its natural length or stretched due to its own weight, i.e., in the neutral state or a state close to this state, the slider 122a is separated from the distal end of the slider receiving portion 124a (the left side end portion in FIG. 4A), for example, by a distance L. Thus, there is looseness between the slider 122a and the slider receiving portion 124a.

The structure of the U-direction side buffer portion 78b is the same as the structure of the U-direction side buffer portion 78a, and so it will not be described here. Further, the structures of the proximal end side traction member 74b, the support portion 76b, the buffer portions 78c and 78d, and the distal end side traction members 80c and 80d, which are present on the D-direction side, are the same as the structures of the proximal end side traction member 74a, the support portion 76a, the buffer portions 78a and 78b, and the distal end side traction members 80a and 80b, which are present on the U-direction side, and so they will not illustrated or described here.

Next, an explanation will be given of functions of the endoscope 10 according to this embodiment.

When the first bending portion 24 is caused to bend, the proximal end side traction member 74a is pulled toward the proximal end side. At this time, the elastic members 84a and 84b are moved toward the proximal end side, while they are, for example, their natural length or stretched due to their own weight, i.e., in the neutral state or a state close to this state.

At this time, since there is play between the sliders 122a and 122b and the slider receiving portions 124a and 124b, when an external force is applied in a state where the bending amount of the first bending portion 24 is small, the second bending portion 26 can be caused to bend in either one of the U-direction and D-direction.

As shown in FIG. 4B, when the first bending portion 24 is caused to bend in the U-direction such that the proximal end side traction member 74a is pulled toward the proximal end side and the elastic members 84a and 84b are extended, the distal end side coupling members 104a and 104b are pulled toward the proximal end side. Accordingly, the slider 122a comes into contact with the distal end of the slider receiving portion 124a. Until this time, there is no tensile force applied to the distal end side traction member 80a. Thus, the slider mechanisms 120a and 120b of the buffer portions 78a and 78b are structured such that the looseness is maximum when the first bending portion 24 is in the straight state, and the looseness becomes gradually smaller as the bending angle of the first bending portion 24 increases from the straight state.

When the proximal end side traction member 74a is further pulled toward the proximal end side from the state shown in FIG. 4B, the elastic members 84a and 84b are extended, and the distal end side coupling members 104a and 104b are pulled toward the proximal end side, as shown in FIG. 4C. Consequently, a tensile force is gradually applied to the distal end side traction members 80a and 80b.

According to this embodiment, only in a range where the bending angle of the first bending portion 24 is large, for example, in the U-direction is a compressive force applied to the second bending portion 26 on the U-direction side to prevent it from bending in the D-direction. Further, only in a range where the bending angle of the first bending portion 24 is large, for example, in the U-direction is the second bending portion 26 prevented from falling in the R-direction and L-direction, i.e., from causing so-called sinking.

Figure 5:
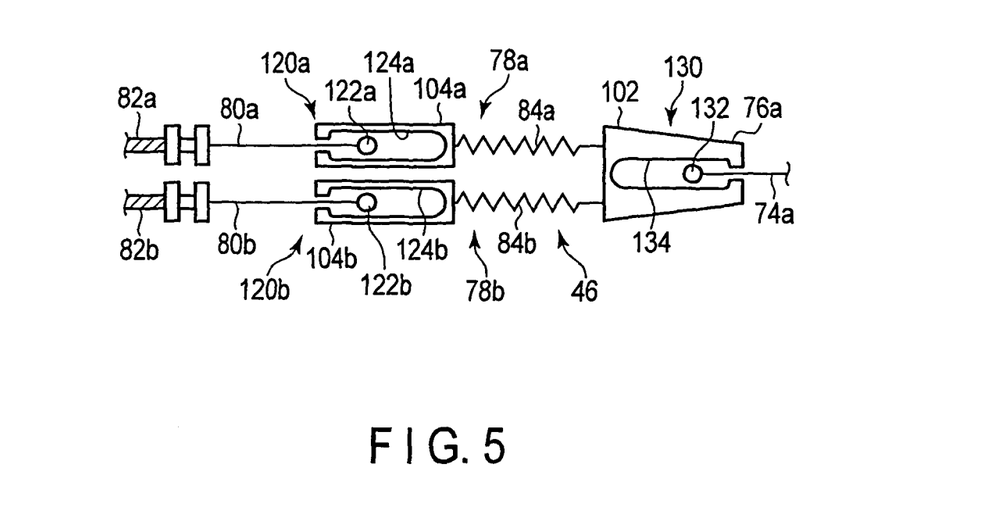
FIG. 5 is a schematic view schematically showing the structure of a buffer portion in the second bending drive mechanism of the endoscope near the boundary between the insertion section and operation section, according to the third embodiment.

Next, an explanation will be given of a third embodiment with reference to FIG. 5. This embodiment is a modification of the first and second embodiments, wherein the same members and members having the same function as those explained in the first and second embodiments are denoted by the same reference numerals, and their detailed description will be omitted. In this embodiment, the buffer portions 76a and 76b are further altered. Specifically, as shown in FIG. 5, the structure of the proximal end side coupling member 102 is arranged in the same way as the distal end side coupling members 104a and 104b.

The buffer portion 78a cooperates with the support portion 76a and the distal end of the proximal end side traction member 74a to form a slider mechanism 130. This slider mechanism 130 includes a slider 132 fixed to the distal end of the proximal end side traction member 74a, and a slider receiving portion (window portion) 134 formed in the proximal end side coupling member 102 and configured to engage with the slider 132 slidably in the axial direction of the proximal end side traction member 74a. In other words, the slider 132 is formed at the distal end of the proximal end side traction member 74a and, for example, it has the same form as that of the sliders 122a and 122b according to the second embodiment. The proximal end side coupling member 102 includes a slider receiving portion (window portion) 134 to engage with the slider 132 of the proximal end side traction member 74a to be relatively movable in the axial direction of the proximal end side traction member 74a. For example, this slider receiving portion 134 has the same form as that of the slider receiving portions 124a and 124b according to the second embodiment.

The slider 132 of the proximal end side traction member 74a can shift relative to the slider receiving portion 134 in the axial direction of the proximal end side traction member 74a, but cannot shift in a direction deviating from the axial direction. Further, the slider 132 engages with the slider receiving portion 134 so as not to come off during the normal action.

As described above, the slider 132 is movable relative to the slider receiving portion 134 at the proximal end side of the buffer portions 78a and 78b, and the sliders 122a and 122b are movable relative to the slider receiving portions 124a and 124b at the distal end side of the buffer portions 78a and 78b. Thus, there is looseness effective until the second sprocket 72 is rotated about its central axis C2 and the second bending portion 26 receives a force transmitted by the rotation.

Next, an explanation will be given of functions of the endoscope 10 according to this embodiment.

When the first bending portion 24 is caused to bend, the proximal end side traction member 74a is pulled toward the proximal end side. At this time, the slider 132 comes into contact with the proximal end of the slider receiving portion 134 of the proximal end side coupling member 102. Then, the elastic members 84a and 84b are moved toward the proximal end side, while they are, for example, their natural length or stretched due to their own weight, i.e., in the neutral state or a state close to this state.

Accordingly, the sliders 122a and 122b come into contact with the distal ends of the slider receiving portions 124a and 124b of the distal end side coupling members 104a and 104b. In a state where the slider 132 is in contact with the proximal end of the slider receiving portion 134, and the sliders 122a and 122b are in contact with the distal ends of the slider receiving portions 124a and 124b, and when the proximal end side traction member 74a is further pulled toward the proximal end side, the elastic members 84a and 84b are extended. Consequently, a tensile force is gradually applied to the distal end side traction members 80a and 80b, as explained with reference to the first and second embodiments.

There is play between the sliders 122a and 122b and the slider receiving portions 124a and 124b, and there is play between the slider 132 and the slider receiving portion 134. Accordingly, when the bending amount of the first bending portion 24 is small (including the straight state), the second bending portion 26 can be caused to bend not only in the U-direction and D-direction but also in either one of the R-direction and L-direction. On the other hand, when the bending amount of the first bending portion 24 is large enough to cancel the play in both of the two slider mechanisms 120a and 130a, a compressive force is gradually applied to the second bending portion 26.

According to this embodiment, only in a range where the bending angle of the first bending portion 24 is large, for example, in the U-direction is a compressive force applied to the second bending portion 26 on the U-direction side to prevent it from bending in the D-direction. Further, only in a range where the bending angle of the first bending portion 24 is large, for example, in the U-direction is the second bending portion 26 prevented from falling in the R-direction and L-direction, i.e., from causing so-called sinking.

In the endoscope 10 according to this embodiment, the sliders 122a and 122b at the proximal ends of the distal end side traction members 80a and 80b are slidable relative to the slider receiving portions 124a and 124b of the distal end side coupling members 104a and 104b. Further, the slider 132 at the proximal end of the proximal end side traction member 74a is slidable relative to the slider receiving portion 134 of the proximal end side coupling member 102. Consequently, as compared with the case explained with reference to the second embodiment, it is possible to expand the adjustment width of the timing at which a compressive force is applied to the second bending portion 26, when the first bending portion 24 is caused to bend.

Next, an explanation will be given of the fourth embodiment with reference to FIGS. 6A and 6B. This embodiment is a modification of the first to third embodiments, wherein the same members and members having the same function as those explained in the first to third embodiments are denoted by the same reference numerals, and their detailed description will be omitted.

Figure 6A:
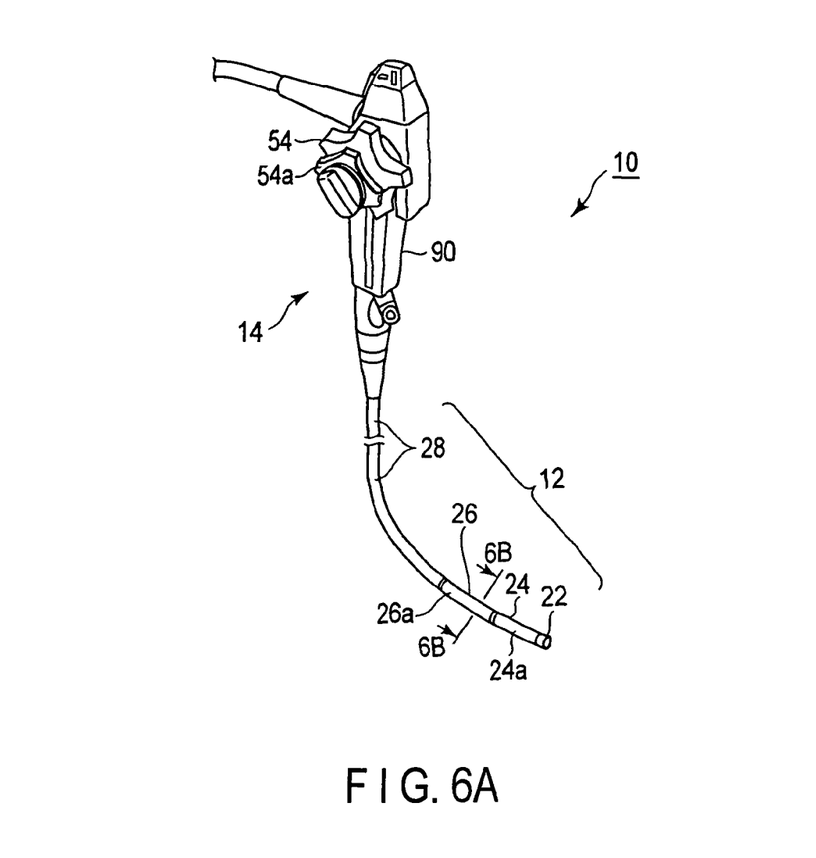
FIG. 6A is a schematic view showing an endoscope according to a fourth embodiment.
Figure 6B:
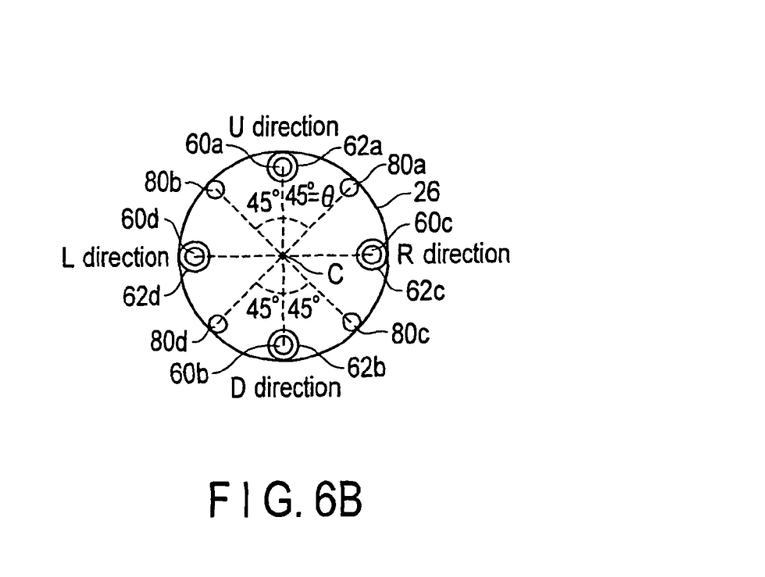
FIG. 6B is a schematically transverse sectional view taken along a line 6B-6B in FIG. 6A.

In the endoscope 10 according to this embodiment, as shown in FIGS. 6A and 6B, the first bending portion 24 and the second bending portion 26 are configured to bend in four directions (U-direction (first direction), D-direction (second direction), R-direction (third direction), and L-direction (fourth direction)).

Specifically, in this embodiment, the first bending drive mechanism 44 includes not only a structure to cause the first bending portion 24 to bend in the U-direction and D-direction, but also a structure to cause the first bending portion 24 to bend in the R-direction and L-direction. Inside the cover 90 of the operation section 14, another sprocket (not shown) is disposed coaxially with the first sprocket 52 and configured to act independently of the first sprocket 52. This other sprocket is coupled to a bending portion operation knob 54a disposed outside the operation section 14 shown in FIG. 6A. This other sprocket is provided with a chain (not shown) that has end portions supporting the proximal ends of angle wires 60c and 60d shown in FIG. 6B. The angle wires 60c and 60d are inserted in coil pipes 62c and 62d. Accordingly, the first bending portion 24 can bend in the four directions.

Also, in this case, the bending mechanism 46 of the second bending portion 26 is driven in conjunction with bending of the first bending portion 24 in the U-direction and D-direction, and it is not driven in response to bending of the first bending portion 24 in the R-direction and L-direction. Accordingly, when the bending portion operation knob 54a is operated to cause the first bending portion 24 to bend in, e.g., the R-direction, the second sprocket 72 is not rotated.

According to this embodiment, when the first bending portion 24 is caused to bend in, e.g., the U-direction, only in a range where the bending angle in the U-direction is large is a compressive force applied to the second bending portion 26 on the U-direction side to prevent it from bending in the D-direction. Further, when the first bending portion 24 is caused to bend in, e.g., the D-direction, only in a range where the bending angle of the first bending portion 24 in, e.g., the D-direction is large is a compressive force applied to the second bending portion 26 on the D-direction side to prevent it from bending in the U-direction. Further, when the first bending portion 24 is caused to bend in, e.g., the U-direction, only in a range where the bending angle of the first bending portion 24 in, e.g., the U-direction is large is the second bending portion 26 prevented from falling in the R-direction and L-direction, i.e., from causing so-called sinking. Similarly, when the first bending portion 24 is caused to bend in, e.g., the D-direction, only in a range where the bending angle of the first bending portion 24 in, e.g., the D-direction is large is the second bending portion 26 prevented from falling in the R-direction and L-direction, i.e., from causing so-called sinking.

[Supplementary Note]

The endoscope according to the first to third embodiment includes an insertion section including a first bending portion and a second bending portion provided on a proximal end side of the first bending portion; a first bending drive mechanism including a first traction member passing inside the second bending portion and configured to cause the first bending portion to bend, and an operation input portion configured to receive an operation input for causing the first bending portion to bend; and a second bending drive mechanism configured to act in response to an operation input to the operation input portion, and including at least one set of second traction members separated from the first traction member by distances almost equal to each other in a circumferential direction of the second bending portion to apply a compressive force to the second bending portion when being pulled.

When the first traction member is pulled to cause the first bending portion to bend, it is possible to apply a compressive force to the at least one set of second traction members, which are separated from the first traction member by distances almost equal to each other in a circumferential direction of the second bending portion. Consequently, when the first bending portion is caused to bend in, e.g., the U-direction, the second bending portion can bend in the U-direction and cannot bend in the D-direction. Further, the second bending portion is prevented from bending in the R-direction or L-direction, because a compressive force is applied to the at least one set of second traction members, which are separated from the first traction member by distances almost equal to each other in a circumferential direction of the second bending portion.

It is preferable that the first bending drive mechanism includes a first rotation axis to rotate and thereby to move the first traction member in its axial direction in response to an operation input to the operation input portion and that the second traction mechanism includes a second rotation axis to rotate and thereby to move the second traction members in its axial direction in accordance with rotation of the first rotation axis.

Accordingly, the second bending drive mechanism can interlock with the first bending drive mechanism to easily apply a compressive force to the second bending portion.

It is preferable that the second traction members include buffer portions to buffer a force with which the second traction members are pulled in their axial directions.

If the buffer portions are included, it is possible to prevent a compressive force being applied to the second bending portion when the first bending portion starts being caused to bend, but to apply a compressive force to the at least one set of second traction members of the second bending portion for the first time when the bending angle of the first bending portion increases suitably to some extent.

It is preferable that the first traction member and the second traction members have a relationship such that the central angles relative to the central axis of the second bending portion are smaller than 90° and almost equal to each other.

For example, when the first traction member is present on the U-direction side, the set of second traction members are present at positions close to the U-direction side and distant from the D-direction side. Further, when the first traction member is present on the D-direction side, the set of second traction members are present at positions close to the D-direction side and distant from the U-direction side. Accordingly, when the first bending portion is caused to bend in the U-direction, a compressive force can be exerted in the UR-direction or UL-direction. Further, when the first bending portion is caused to bend in the D-direction, a compressive force can be exerted in the DR-direction or DL-direction.

The central angles preferably have a relationship of almost 45°.

In this case, when the first bending portion is caused to bend in, e.g., the U-direction, the compressive force component in the U-direction and the compressive force components in the R-direction and/or L-direction can be almost the same as each other. Further, when the first bending portion is caused to bend in, e.g., the D-direction, the compressive force component in the D-direction and the compressive force components in the R-direction and/or L-direction can be almost the same as each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope for use with a subject, the endoscope comprising:
   an insertion section capable of being inserted into the subject, the insertion section including: (i) a first bending portion configured to bend in an upward direction and a downward direction, and (ii) a second bending portion provided on a proximal end side of the first bending portion and configured to bend in the upward direction and the downward direction and in a right direction and a left direction along a circumferential direction of the upward direction and the downward direction;
   an upward direction side traction member that passes inside the second bending portion and is fixed to the first bending portion and which is configured to bend the first bending portion in the upward direction;
   a first distal end side traction member fixed to a position at a side of the upward direction of the second bending portion, the first distal end side traction member being separated from the upward direction side traction member toward the right direction, the first distal end side traction member passing inside the insertion section, and the first distal end side traction member pulling the second bending portion so as to generate a traction force in a direction between the upward direction and the right direction;
   a second distal end side traction member fixed to a position at a side of the upward direction of the second bending portion, the second distal end side traction member being separated from the upward direction side traction member toward the left direction, the second distal end side traction member passing inside the insertion section, and the second distal end side traction member pulling the second bending portion so as to generate a traction force in a direction between the upward direction and the left direction;

a first support portion operatively coupling the upward direction side traction member to the first distal end side traction member and the second distal end side traction member, the first support portion pulling the first distal end side traction member and the second distal end side traction member when the upward direction side traction member is pulled:

a downward direction side traction member that passes inside the second bending portion and is fixed to the first bending portion, the downward direction side traction member being configured to bend the first bending portion in the downward direction;

a third distal end side traction member fixed to a position at a side of the downward direction of the second bending portion, the third distal end side traction member being separated from the downward direction side traction member toward the right direction, the third distal end side traction member passing inside the insertion section, and the third distal end side traction member pulling the second bending portion on as to generate a traction force in a direction between the downward direction and the right direction;

a fourth distal end side traction member fixed to a position at a side of the downward direction of the second bending portion, the fourth distal end side traction member being separated from the downward direction side traction member towards the left direction, the fourth distal end side traction member passing inside the insertion section, and the fourth distal end side traction member pulling the second bending portion so as to generate a traction force in a direction between the downward direction and the left direction; and a second support portion operatively coupling the downward direction side traction member to the third distal end side traction member and the fourth distal end side traction member, the second support portion pulling the third distal end side traction member and the fourth distal end side traction member when the downward direction side traction member is pulled.

2. The endoscope according to claim 1, wherein the first distal end side traction member and the second distal end side traction member are separated from the upward direction of the second bending portion by distances almost equal to each other in a circumferential direction.

3. The endoscope according to claim 2, wherein the upward direction side traction member and the first and second distal end side traction members have a relationship such that central angles relative to a central axis of the second bending portion are smaller than 90° and almost equal to each other.

4. The endoscope according to claim 3, wherein the central angles have a relationship of almost 45°.

5. The endoscope according to claim 1, comprising a buffer portion configured to buffer a traction force of each of the first distal end side traction member and the second distal end side traction member.

6. The endoscope according to claim 5, wherein the buffer portion includes an elastic member.

7. The endoscope according to claim 1, further comprising:
a proximal end side traction member configured to pull the distal end side traction member and the distal end side traction member in conjunction with the upward direction side traction member z when the upward direction side traction member is pulled and the first bending portion is bent in the upward side,
a first sprocket rotatable to pull the upward direction side traction member, and
a second sprocket in conjunction with the first sprocket, which is rotatable to pull the proximal end side traction member.

8. The endoscope according to claim 1, further comprising:
another proximal end side traction member configured to pull the third and fourth distal end side traction members among the first to fourth distal end side traction members in conjunction with the downward direction side traction member when the downward direction side traction member is pulled and the first bending portion is bent in the downward direction.

9. The endoscope according to claim 8, further comprising:
a first sprocket rotatable to pull the upward direction side traction member and the downward direction side traction member; and
a second sprocket in conjunction with the first sprocket, which is rotatable to pull the proximal end side traction member and the another proximal end side traction member.

10. The endoscope according to claim 1, further comprising:
a slider mechanism fixed to the first distal end side traction member such that the first distal end side traction member is moveable relative to the first support portion.

11. The endoscope according to claim 1, further comprising:
an engagement portion disposed on the upward direction side traction member, and being configured to set an initial tension of the upward direction side traction member.

* * * * *